(12) United States Patent
Idstrom

(10) Patent No.: US 9,993,623 B2
(45) Date of Patent: Jun. 12, 2018

(54) GUIDEWIRES WITH VARIABLE RIGIDITY

(71) Applicant: Mark Edman Idstrom, Kansas City, MO (US)

(72) Inventor: Mark Edman Idstrom, Kansas City, MO (US)

(*) Notice: Subject to any disclaimer, the term of this patent is extended or adjusted under 35 U.S.C. 154(b) by 744 days.

(21) Appl. No.: 14/263,674

(22) Filed: Apr. 28, 2014

(65) Prior Publication Data

US 2015/0306353 A1    Oct. 29, 2015

(51) Int. Cl.
*A61M 25/09*    (2006.01)

(52) U.S. Cl.
CPC ..... *A61M 25/09* (2013.01); *A61M 2025/0915* (2013.01); *A61M 2025/09091* (2013.01); *A61M 2025/09175* (2013.01)

(58) Field of Classification Search
CPC .......... A61M 25/09; A61M 2025/0915; A61M 2025/09091; A61M 29/00; A61M 2025/0177; A51M 2025/09175; A61F 2/07; A61B 18/245
USPC ...... 600/139, 144, 146, 140, 114; 604/95.01
See application file for complete search history.

(56) References Cited

U.S. PATENT DOCUMENTS

| | | | | |
|---|---|---|---|---|
| 4,329,980 A * | 5/1982 | Terada | ............... | A61B 1/00078 600/140 |
| 6,610,007 B2 * | 8/2003 | Belson | ................. | A61B 1/0053 600/144 |
| 8,092,374 B2 * | 1/2012 | Smith | ................ | A61B 1/00078 600/114 |
| 2005/0038406 A1 * | 2/2005 | Epstein | ................. | A61M 25/00 604/500 |
| 2007/0043261 A1 * | 2/2007 | Watanabe | .......... | A61B 1/00071 600/144 |

* cited by examiner

*Primary Examiner* — Manuel Mendez

(57) ABSTRACT

Guidewires are disclosed being configured to achieve variable rigidity to facilitate percutaneous exploration and the traversal of overlying elements such as catheters, for instance in performing the Seldinger technique. Embodiments of guidewires comprise sheaths and cores configured to be tightened together to achieve stiffness of the guidewire. Embodiments further include cores having an axial passage, along with one or more sections capable of independent activation to achieve variable rigidity. Embodiments also include guidewires comprising combinations of solid, wound metallic, or polymeric coils, or woven meshes, with attached or detached polymer coatings. Cores may be configured to increase or decrease pressure, pass acoustic, ultrasonic or other mechanical energy, pass one or more metallic cores to interact with the distal mechanical elements, or as a channel to pass wires to activate the distal materials in the sections and distal tip.

20 Claims, 10 Drawing Sheets

GUIDEWIRES WITH VARIABLE RIGIDITY

BACKGROUND

Minimally invasive surgical techniques are an important aspect of medical procedures. Such procedures often require access to blood vessels, structures, organs, or cavities from small apertures at a distance. For example, in certain angioplasty procedures, from a small incision in the wrist or groin, a catheter may be advanced through the cardiovascular to a blocked or restricted artery. A balloon attached to the catheter, when positioned within the blockage, may then be inflated to radially expand against the restriction to enlarge the opening and increase the blood flow. Balloon catheters include over-the-wire designs requiring little support or control, allowing the placement of a small steerable wire through the restriction facilitating the catheter can track the wire across the blockage. To reach areas of blood vessels restriction, guidewires often must traverse shallow or sharp turns, circuitous paths, pass competing branches, and cross disease and/or narrowed vessels. This may be accomplished by an operator advancing and withdrawing a guidewire while rotating a pre-formed tip into a favorable position while observing via fluoroscopy. As the guidewire advances deeper into the vessels in smaller and more diseased segments, increased resistance occurs between the guidewire and the blood vessel walls.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments include guidewires having variable rigidity. In certain embodiments, variable rigidity may be achieved via cores comprising solid wires or walled tubes. Cores may include coatings and may be stiffer than other sections of the guidewire, and function to guide and support a catheter (or other element) and transmit action and support rotation from an operator to the distal end. Intermediate sections may be interspersed axially and be more or less flexible than the core. In certain embodiments, variable rigidity may be achieved via a sheath disposed around a core. In one example, a sheath may comprise a coil or spring surrounding a core. Intermediate sections may transmit motion and rotation in addition to guiding an overlying catheter (or other element). Flexibility may be complimentary to permit the guidewire to conform to the curvature and tortuosity of the vasculature. A distal tip may connect via a distal joint, and may additionally include a curve allowing the guidewire to be directed from an operator.

DETAILED DESCRIPTION

Figure 1A:
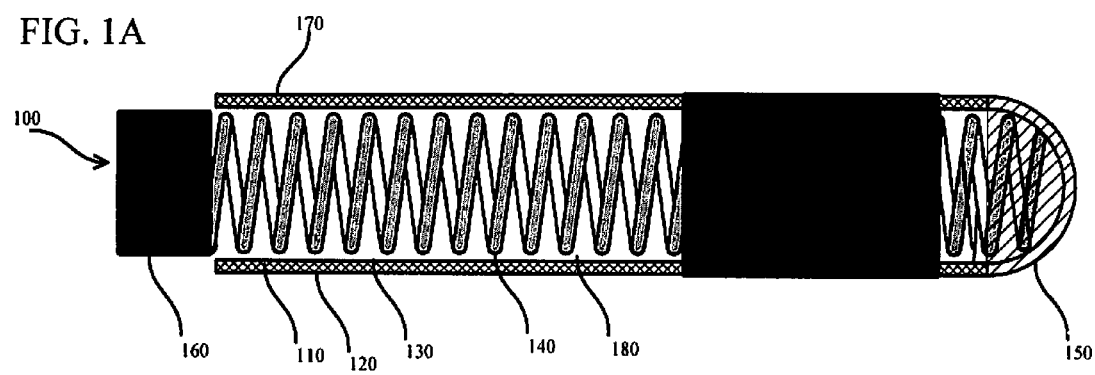
FIG. 1A shows a cross sectional view of an exemplary embodiment of the present invention.

The subject matter of the present invention is described with specificity to meet statutory requirements. The description itself is not intended to limit the scope of this patent, however. Rather, the inventor has contemplated that the claimed subject matter might also be embodied in other ways, including via different components or combinations of components similar to the ones described in this document, as well as embodiments comprising methods or systems, including embodiments in conjunction with other present or future technologies.

In general, the more tortuous and acutely angled the sections of vasculature to traverse, the softer the guidewire required to reach a target. However, stiffer guidewires may be advantageous for use with overlying elements (such as a catheter) because such guidewires allow the overlying elements to more efficiently follow and reach a target. For instance, a catheter may be prevented from reaching the target when used over a soft guidewire because the catheter may eject a soft guidewire from the vessel, or dig into the vessel at a sharp curve, rather than follow the guidewire. This may be addressed via serially exchanging from the initial soft wire, to a soft catheter, to a firmer guidewire, then a firmer catheter, and so on until an adequately firm supporting guidewire is in place. These serial exchanges are time consuming, can cause vessel injury, require extra supplies, can lead to contamination at the insertion site, and can stimulate spasm in the vessel ultimately leading to the failure of the procedure. Stiff guidewires may have disadvantages in taking tortuous anatomy and forcing it to conform to the relatively straight shape of the guidewire, which may stimulate spasm of the vessel, distort the anatomy (which changes the location of the target), and increase the risk of perforation and vessel injury.

Embodiments of the present invention include guidewires facilitating the maintenance of control and flexibility for access to targets (such as percutaneous medical targets), and which also may be selectively stiffened to support and facilitate the guidance of an element (such as a catheter) to the target.

In one embodiment in accordance with the present invention, a guidewire is disclosed comprising a core, and a sheath disposed around the core. The sheath is configured to tighten to the core. As used herein, when elements are described as tightening or being tightened to another element, it is contemplated that in some instances, only portions of the elements may be tightened together, rather than the entire elements. It is also contemplated that entire elements may be tightened together. Both such configurations are contemplated as being within the scope of the present invention. Further, the guidewire may comprise a means for tightening the sheath to the core. Additionally, the core may comprise a coil. The guidewire may by configured to operatively stiffen via a suction element configured to retractably tighten the sheath to the core. As used herein, when guidewires are described as "stiffening," being "stiffened," or becoming "stiff," etc., it is contemplated that only portions of the guidewire may become stiffened (rather than the entire guidewire). It is also contemplated that the entire guidewire may be stiffened in configurations. Such embodiments are within the bounds contemplated by the inventor. Keeping with the previous example, additionally or alternatively, the sheath may comprise a helical braid, which may be tightened to the core via the application of an axially retracting force. Still in addition or in the alternative, the sheath may comprise an outer coil, which may be tightened to the core via the application of a force, such as a rotational or retracting force. These, or other configurations or means, may tighten the sheath to the core, stiffening the guidewire.

In another embodiment in accordance with the present invention, a guidewire is disclosed. The guidewire includes a core. The guidewire further includes a sheath disposed around the core. In embodiments, the core may be configured to be tightened to the sheath. In certain embodiments, the guidewire includes a means for tightening the core to the sheath. For instance, the core of the guidewire may comprise a coil, and the coil may be twisted to tighten it to the sheath, which may stiffen the guidewire. The guidewire may additionally include a tip having an inner surface, and the core may be fixed to the inner surface of the tip. This configuration allows the coil to be twistingly expanded when rotation is applied. The core may also comprises a helically wound braid, where the core is tightened to the sheath via the application of axial force to the helically wound braid.

In yet another embodiment in accordance with the present invention, a guidewire is disclosed that includes a core having a first end, a second end distal from the first end, an outer surface, and an intermediate section. The second end defines a tip, the tip being optionally configured to facilitate percutaneous exploration. The intermediate section may further be configured to increase in rigidity upon activation. The guidewire may also be configured to provide a pathway for an overlying element, such as a catheter. The outer surface may be selected from percutaneously compatible materials. The core may also comprise an electroactive material, such as an electroactive polymer. The electroactive material may be electrically stimulated to increase the rigidity of portions of the guidewire. Alternatively or additionally, the core may comprise a coil, and the intermediate section may be configured for activation via rotation of the coil. Still alternatively or additionally, the shaft may include a non-Newtonian fluid, and wherein the intermediate section is configured for activation via mechanical stimulation of the non-Newtonian fluid. One example of such a mechanical stimulation includes oscillatory stimulation.

In another aspect of embodiments, a guidewire comprise a core having an axial passage; an intermediate section comprising a coil coupled to a polymer membrane sheath; and a blunt tip coupled to the polymeric membrane and wound coil. The guidewire may be configured to cause the sheath and coil to interact and stiffen the guidewire. This may be accomplished via induced positive pressure in the axial passage, negative pressure in the axial passage, combinations of positive and negative pressures, or other means. It will be understood that various other means of achieving variable rigidity are within the bounds of the present inventions. As one example, another aspect of embodiments include add coating to the inner coil, or would add a wound coil to the outer membrane.

Another aspect of embodiments includes a guidewire comprising a core, the core being hollow, and wherein the inner portion of the core includes stiffening elements for selectively stiffening the guidewire. For instance, stiffening elements may be chosen from the group consisting of linear wires, polymeric fibers, metallic granules, or polymeric granules. As an example of means for stiffening the guidewire, a change from positive to negative pressure may create an interaction between the polymeric membrane and the central solids leading to a stiffening of the guidewire.

In still another aspect of embodiments, a guidewire includes a core, one or more intermediate sections, and a tip. The core (and intermediate sections in certain instances) may comprise a wound coil. The wound coil includes an inner portion, and may be configured to retain an inflatable element (such as a balloon) within the inner portion. Such an inflatable element, when inflated, may be configured to expand radially against the wound coil, stiffening the guidewire. When stiffened, the guidewire may advantageously provide a path for overlaying elements (such as a catheter, grapple, hook, optical unit, or other surgical element) to traverse. When necessary, the inflatable element may be deflated, reducing the stiffness of the guidewire, facilitating the further guidance or retraction of the guidewire. In alternate configurations, the inner portion of the wound coil may retain materials which, when activated (via mechanical, chemical, or electrical means), hardens, stiffens, or swells, stiffening the guidewire. In yet another aspect, the inner portion may retain additional coils, woven meshes, or other mechanical elements attached to the inner portion that may be expanded against inner portion when activated, stiffening the guidewire. The activation may be achieved by through motion or rotation on the wire or mesh. Depending on the configuration of the coil or mesh, the guidewire may be stiffened from proximal to distal, or distal to proximal.

Figure 1B:
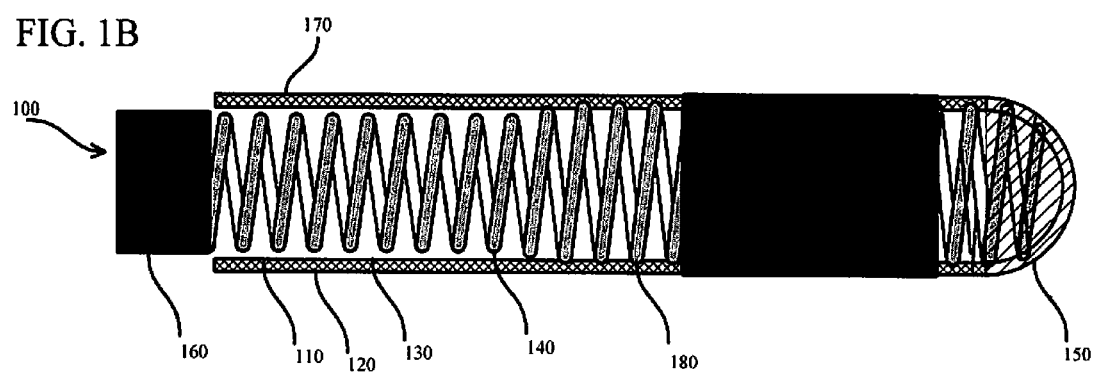
FIG. 1B shows another cross sectional view of an exemplary embodiment of the present invention.

Having briefly described an overview of embodiments of the present invention, exemplary guidewires are described. Referring to FIG. 1A, a cross sectional view of guidewire 100 is shown. Guidewire 100 includes sheath 110, which has outer surface 120 and inner surface 130. Guidewire 100 further includes first end 170 and second end 150, first end 170 being distal from second end 150. In this instance, second end 150 defines a tip. Guidewire 100 further includes core 180, the core comprising coil 140 and shaft 160. Coil 140 and shaft 160 are coupled together. In this instance, shaft 160 and coil 140 comprise a means for tightening to sheath 110 via rotational force applied to shaft 160. Guidewire 100 is configured such that coil 100 may be tightened via the application of rotational force via shaft element 160. Referring now to FIG. 1B, another cross sectional view of guidewire 100 is illustrated. In this instance, coil 140 is shown having been rotationally expanded so as to tighten to sheath 110. (As can be seen, guidewire 100 may be stiffened along portions, rather than entire length of guidewire 100.) Guidewire 100 operatively stiffens when coil 140 is tightened against sheath 110, facilitating the guidance of an overlying element toward a target. For instance, as with the guidance of a medical element—such as a catheter—in performing the Seldinger technique, or other techniques.

Figure 2A:
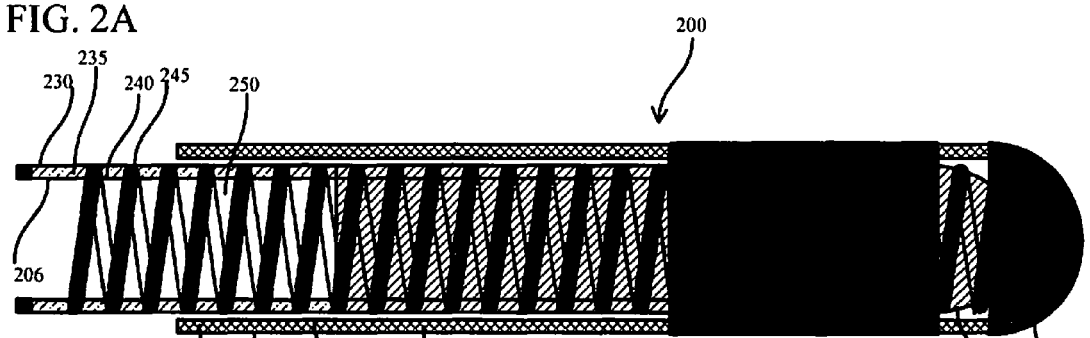
FIG. 2A depicts a cross sectional view of an exemplary embodiment of the present invention.
Figure 2B:
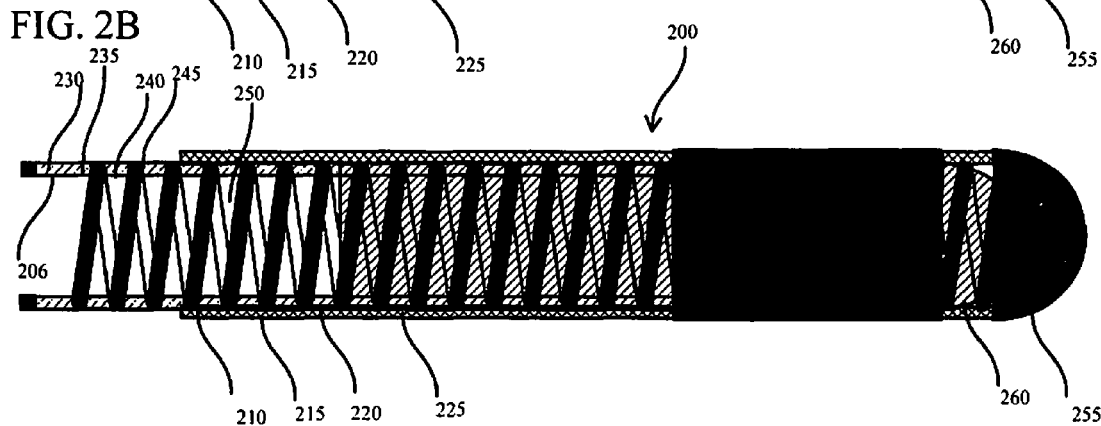
FIG. 2B depicts another cross sectional view of an exemplary embodiment of the present invention.

Referring now to FIG. 2A, a cross sectional view of a guidewire 200 is shown. Guidewire 200 includes sheath 210, which has outer surface 215, inner surface 220, and inner portion 225. In some embodiments, inner portion 225 includes an electrically conductive material or structures. Guidewire 200 further includes core 230, which comprises covering 235 having an inner surface 240 and outer surface 245. Inner surface 245 defines an interior, which houses coil 250, which in some embodiments is electrically conductive. At the distal end of guidewire 200 is tip 255, and, in the particular configuration depicted, tip 260 of core 230. The boundary between sheath 210 and core 230 define an interface. Various means may be employed to tighten sheath 210 to core 230 (wholly or in portions). For instance, suction may be applied to the interface, drawing sheath 210 toward core 230, stiffening guidewire 200. Another means includes applying rotational force to coil 250, which serves to expand coil 250 along with core 230 until outer surface 245 contacts inner surface 220, stiffening guidewire 200. Yet another means includes providing a positive pressure to the cavity defined by inner surface 240, inflatably expanding core 230 to tighten to sheath 210. Still another means, in the case where core 230 includes electrically conductive material and sheath 210 comprises electrically conductive material, includes inducing attractive magnetic forces between core 230 and sheath 210. For instance, differing electrical currents may be applied to core 230 and sheath 210, inducing attractive magnetic fields such that sheath 210 and core 230 tighten together, stiffening guidewire 200. Various other mechanical, electrical, magnetic, and chemical means for tightening sheath 210 and core 230 together may be apparent to those of skill in the art, and are contemplated as within the bounds of the present invention. FIG. 2B depicts guidewire 200 wherein sheath 210 and core 230 are tightened together. Additionally, configurations include selectively applying tightening means to portions of sheath 210 and core 230, operatively stiffening intermediate sections of guidewire 200. For instance, guidewire 200 may include multiple intermediate sections, each defined by separate activation sections. For instance, activation sections may comprise different circuit paths electrically accessible from a proximal end of guidewire 200. When a current is applied to a particular circuit path, the intermediate section defined by that circuit path may be activated, stiffening that intermediate section of the guidewire.

Figure 3:
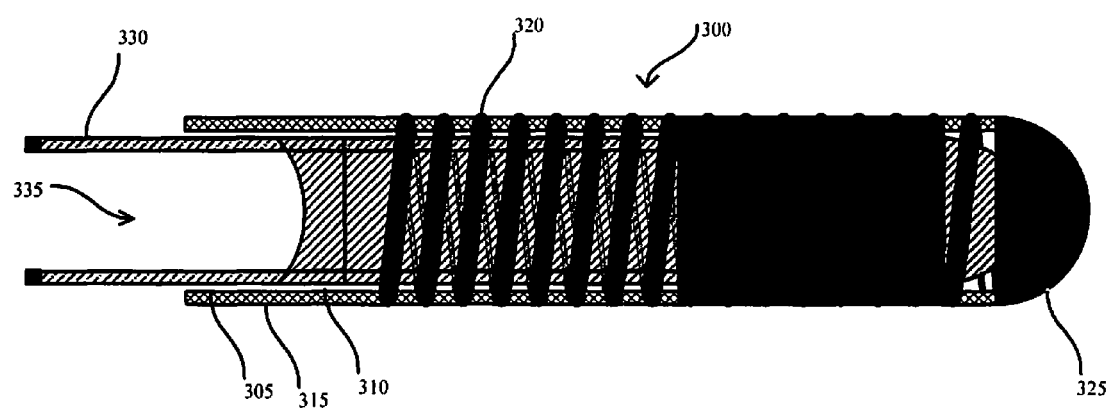
FIG. 3 depicts still another cross sectional view of an exemplary embodiment of the present invention.

FIG. 3 will now be discussed, which depicts a cross sectional view of guidewire 300. Guidewire 300 includes sheath 305, which comprises inner surface 310, outer surface 315, and tip 325. Tip 325 may be fashioned to provide a blunt end for guidewire 300, which may be advantageous for percutaneous insertion and exploration of intravenous, intra-arterial, or intra-cavity exploration to reach a medical target. Inner surface 310 defines an interior, which houses core 330. In the depicted embodiment, sheath 305 is coupled to coil 320, which provides structure and a configuration for tightening sheath 305 to core 330 (for instance by applying rotational force to coil 320 to stiffen guidewire 300). Core 330 defines interior 335. In some embodiments, core 330 comprises an inflatable element, which comprise a means for tightening core 330 to sheath 305. Means for tightening core 330 to sheath 305 further include applying positive pressure to interior 335, (such as by expanding core 330 such as to tighten to sheath 305). Outer surface 315 may comprise a variety of materials, or coatings, advantageous for percutaneous insertion.

Figure 4:
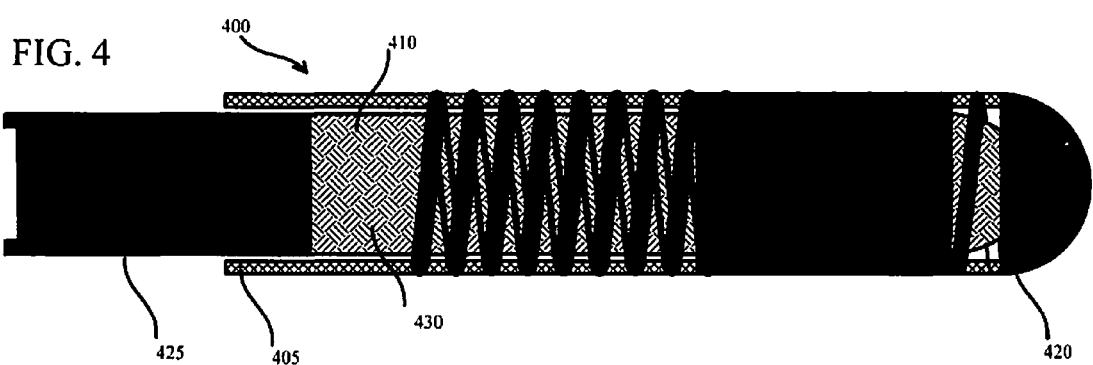
FIG. 4 illustrates still another cross sectional view of an exemplary embodiment of the present invention.

Turning now to FIG. 4, a cross sectional view of guidewire 400 is depicted. Guidewire 400 comprises sheath 405, which includes tip 420. Sheath 405 defines an interior, which houses core 410. In the embodiment depicted, core 410 comprises a helical braid, such as a biaxial braid (as seen in, for example, Chinese finger traps). Core 410 further comprises pusher 425 and intermediate section 430. An axial force may be applied to pusher 425, radially expanding core 410 due to the biaxial weave composition, tightening core 410 against sheath 405, increasing the rigidity of guidewire 400. Additional means for tightening sheath 405 to core 410 are contemplated by the inventor, as well as additional means for tightening core 410 to sheath 405—such as differing configurations of pushers, coils, sheaths, cores, and combinations thereof.

Figure 5A:
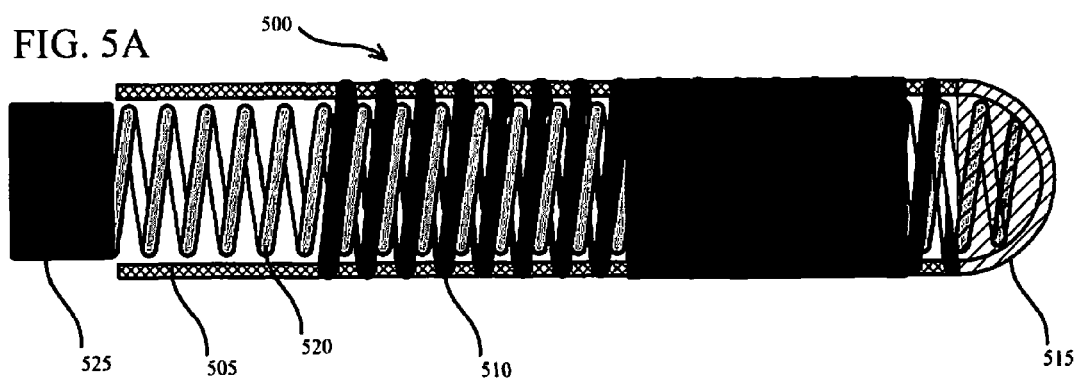
FIG. 5A illustrates a cross sectional view of an exemplary embodiment of the present invention.
Figure 5B:
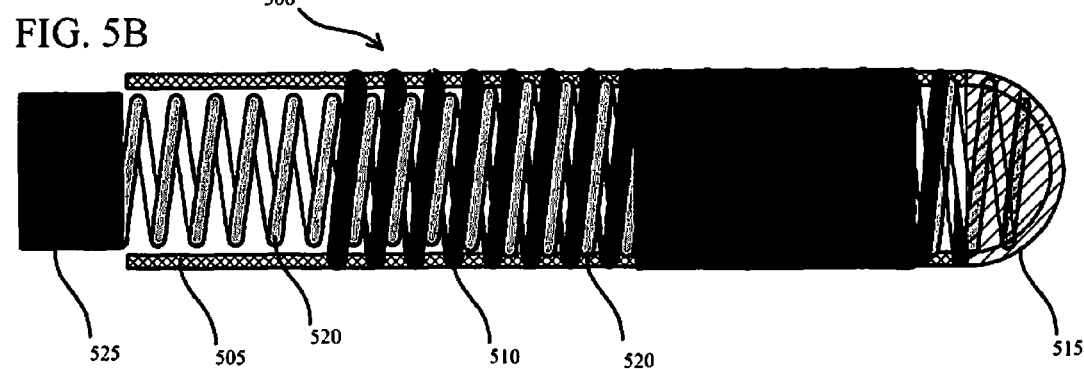
FIG. 5B illustrates a cross sectional view of an exemplary embodiment of the present invention.

Moving on to FIG. 5A, a cross sectional view depicts another aspect in accordance with embodiments. Guidewire 500 comprises sheath 505 having tip 515. Sheath 505 defines a interior and is coupled to coil 510. Core 520 comprises a coil, which is operatively interlinked with coil 510. Core 520 is coupled to rotational element 525, which is configured to facilitate the application of rotational force to coil 520, activating guidewire 500 to increase rigidity. Means for tightening core 520 to sheath 505 include the coil composition of core 520 and coil 510, as well as rotational element 525 (though the latter may or may not be necessary, or may comprise various alternative configurations). FIG. 5B illustrates an embodiment wherein core 520 is tightened to sheath 505, also illustrating that a distal first section may be tightened independently of a proximal second section.

Figure 6A:
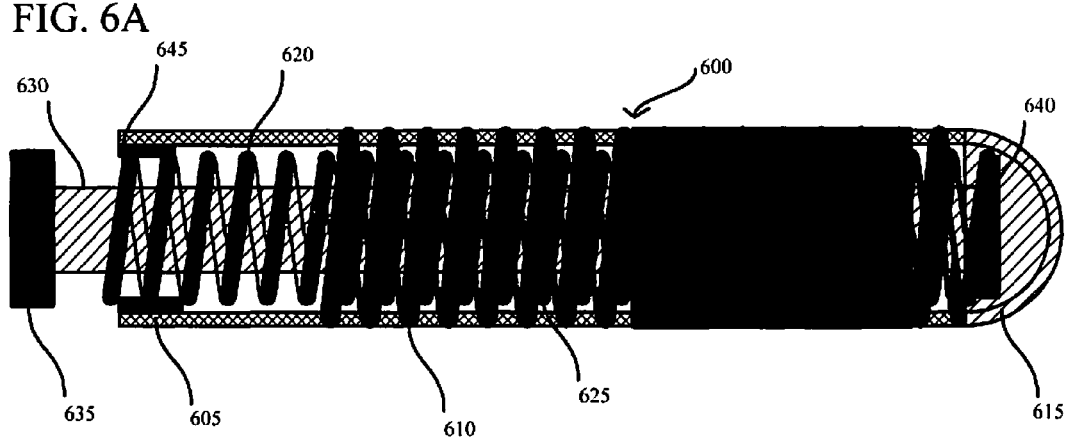
FIG. 6A depicts a cross sectional view of an exemplary embodiment of the present invention.
Figure 6B:
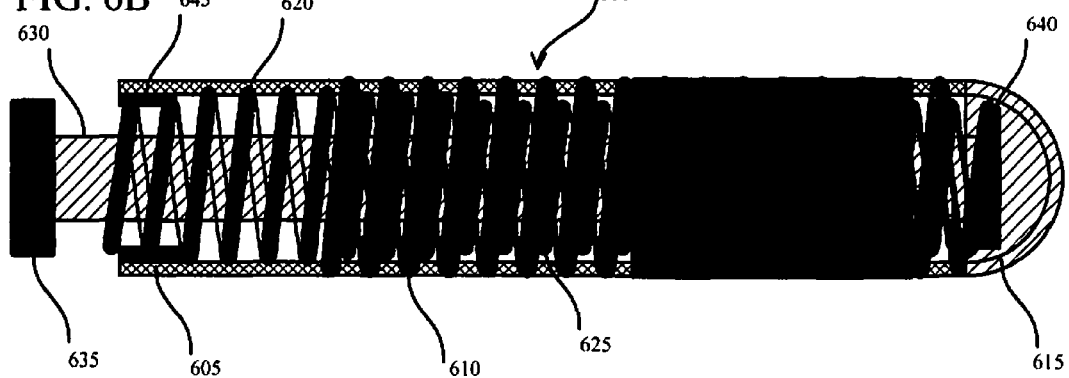
FIG. 6B depicts a cross sectional view of an exemplary embodiment of the present invention.

Turning now to FIG. 6A, a cross sectional view of guidewire 600 is depicted. Guidewire 600 comprises sheath 605, which defines distal tip 615. Distal tip 615 may comprise a soft material formed into a blunt shape, preventing puncture as guidewire 600 is operated for percutaneous exploration. Sheath 605 further comprises coil 610, which is configured to provide structure to sheath 605, as well as to allow sheath 605 to be operatively tightened to core 620. Core 620 comprises coil 625, which is interlinked with coil 610. Core 620 further comprises shaft 630, which is coupled at portion 640 to coil 625, and coil 625 is further coupled to sheath 605 at end 645. This configuration advantageously allows rotational force on shaft 630 to be translated to coil 625 near end 645, radially expanding core 620 to tighten to sheath 605 near end 645, operatively guided via coil 610. Grip 635 provides traction in order to apply rotational force to coil 625 via shaft 630. Coil 625 thus comprises a means for tightening core 620 to sheath 605, operatively stiffening guidewire 600. FIG. 6B depicts guidewire 600 wherein a proximal first section is tightened independently of a distal second section.

Figure 7A:
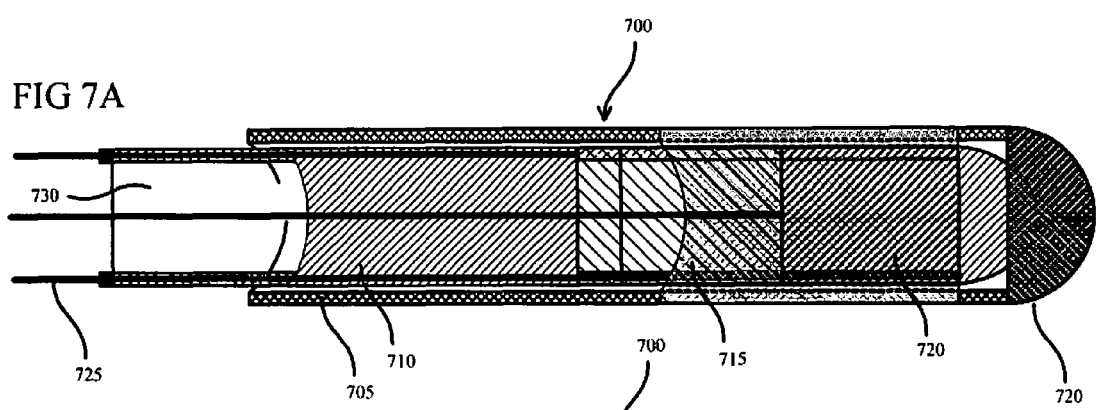
FIG. 7A shows another cross sectional view of an exemplary embodiment of the present invention.
Figure 7B:
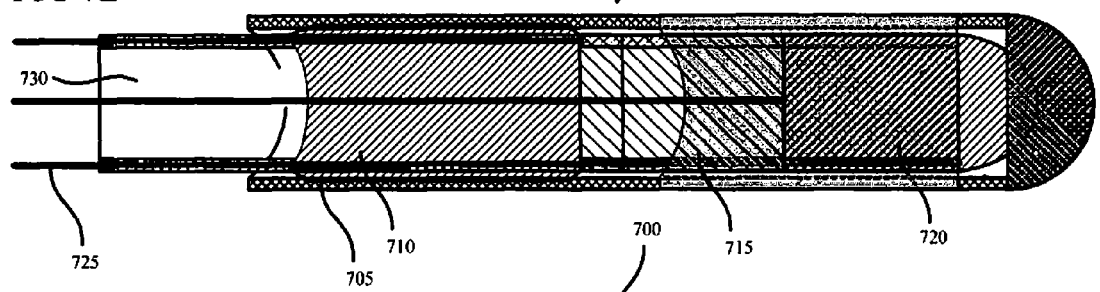
FIG. 7B illustrates another cross sectional view of an exemplary embodiment of the present invention.
Figure 7C:
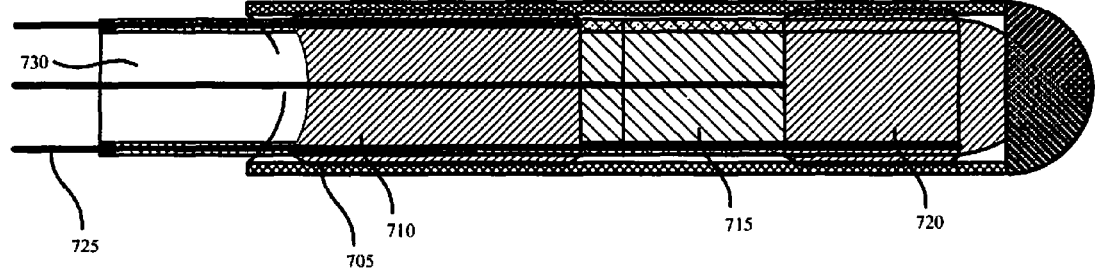
FIG. 7C illustrates still another cross sectional view of an exemplary embodiment of the present invention.

FIG. 7A illustrates a cross sectional view of guidewire 700, which illustrates a configuration comprising multiple intermediate sections, each capable of being independently stiffened. Guidewire 700 comprises core 725, which comprises an electrically conductive cylindrical structure that may be magnetically activated via electrical stimulation. Guidewire 700 further comprises sheath 705. Core 725 further comprises first intermediate section 710, second intermediate section 715, and third intermediate section 720. Each of these intermediate sections is electrically coupled to end 730 via independent circuits, such that each intermediate section is capable of being electrically stimulated independently of other intermediate sections. For instance, electrical stimulation may be applied to the circuit path coupled to second intermediate section 715 independently of first intermediate section 710 and third intermediate section 720, inducing a magnetic activation to attract second intermediate section 715 to sheath 705. In such a case, only second intermediate section 715 is electrically activated, while first intermediate section 710 and third intermediate section 720 remain non-activated. If desired, because the intermediate sections are independently capable of activation, first intermediate section 710 and third intermediate section 720 may also be electrically activated, stiffening those sections in addition or in the alternative to second intermediate section 715. For illustration, FIG. 7B depicts a further cross sectional view of guidewire 700 wherein first intermediate section 710 is magnetically activated via electrical stimulation, tightening first intermediate section 710 to sheath 705, stiffening guidewire 700 around first intermediate section 710. As can be seen, second intermediate section 715 and third intermediate section 720 are not magnetically activated in FIG. 7B, and as such, these intermediate sections are not tightened to sheath 705. As another illustration, FIG. 7C depicts a further scenario wherein third intermediate section 720 is additionally electrically stimulated, magnetically activating third intermediate section 720 and tightening it to sheath 705 as well as first intermediate section 710 (while second intermediate section 715 remains un-activated). Thus, it can be seen that each intermediate section may be independently activated, tightening independent sections of guidewire 700 as desired. As will be apparent, any number of intermediate sections may be activated in various combinations, achieving stiffness of portions of guidewire 700 according to desires. These and other configurations and means for tightening core 725 to sheath 705 are within the bounds of the invention, including having intermediate sections of sheath 705 capable of independent activation to be tightened to core 725. Still another means for said tightening involves intermediate sections independently coupled to end 730 via separate coil partitions, each intermediate section configured for activation via independent applications of mechanical or electrical force.

Figure 8:
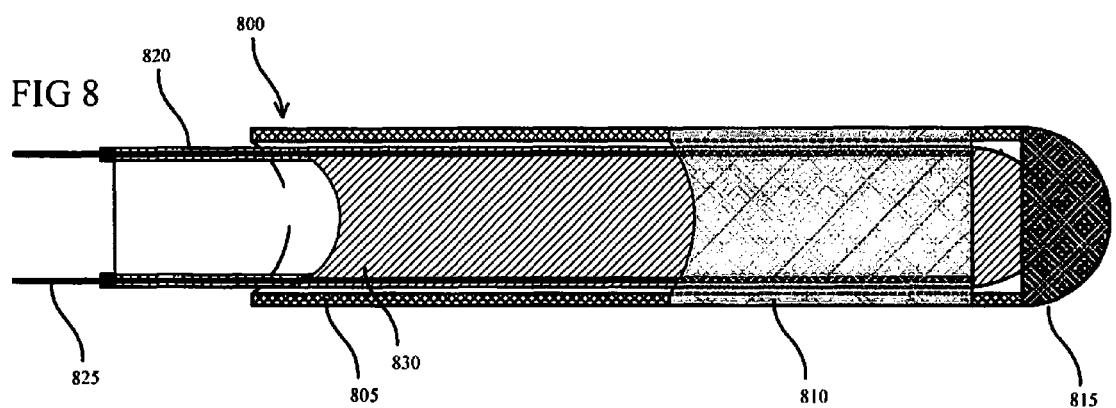
FIG. 8 shows a cross sectional view of an exemplary embodiment of the present invention.

Turning now to FIG. 8, cross sectional view of guidewire 800 is depicted. Guidewire 800 comprises sheath 805, which may comprises coil 810. In this instance, coil 810 provides structure to a portion of sheath 805, but other elements may be operational to provide structure to sheath 805, including the material from which sheath 805 is constructed. For instance, sheath 805 may be constructed from polymer materials providing appropriate stiffness and flexibility. Sheath 805 further comprises tip 815, which comprises a soft material appropriate for percutaneous insertion and exploration. Guidewire 800 further comprises core 820, which comprises electrode 825, which traverses core 820 and may advantageously follow a path covering an appropriate cross-sectional area of core 820. Core 820 further comprises an interior, which houses electroactive material 830. Electroactive material 830 may be electrically stimulated via electrical activation of electrode 825. Various electroactive materials may be known to those of skill in the art, and include, for instance, electrically activated gels, piezoelectric materials in various structural configurations, or carbon nanotube materials.

Figure 9:
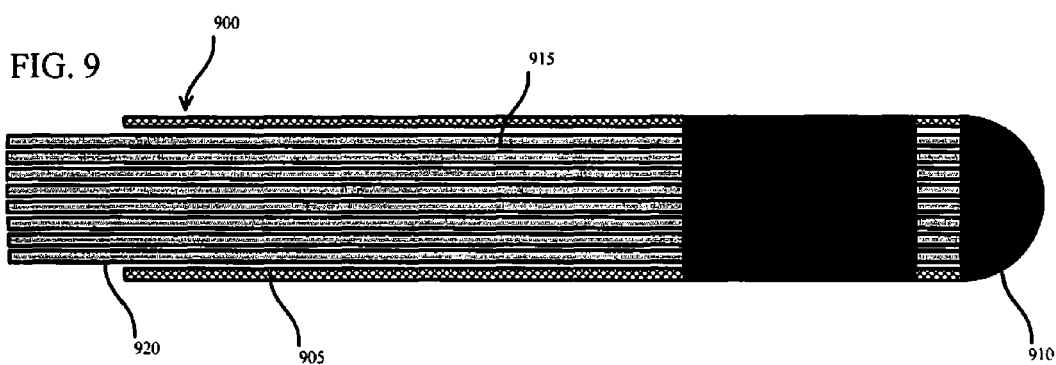
FIG. 9 depicts another cross sectional view of an exemplary embodiment of the present invention.

FIG. 9 depicts a cross sectional view of guidewire 900, which comprises sheath 905. Sheath 905 defines tip 910, which is configured for percutaneous exploration. Guidewire 900 further comprises core 915, which in guidewire 900 comprises multiple, flexible fibers operational to provide structure to guidewire 900 when used for medical or other techniques. The flexible fibers comprising core 915 may be structured in various manners, such as braided, threaded, twisted, or straightened. Interior space 920 may be operative to have a sectional force applied, tightening sheath 905 to core 915, operatively stiffening guidewire 900, or alternatively tightening core 915 to sheath 905.

Figure 10A:
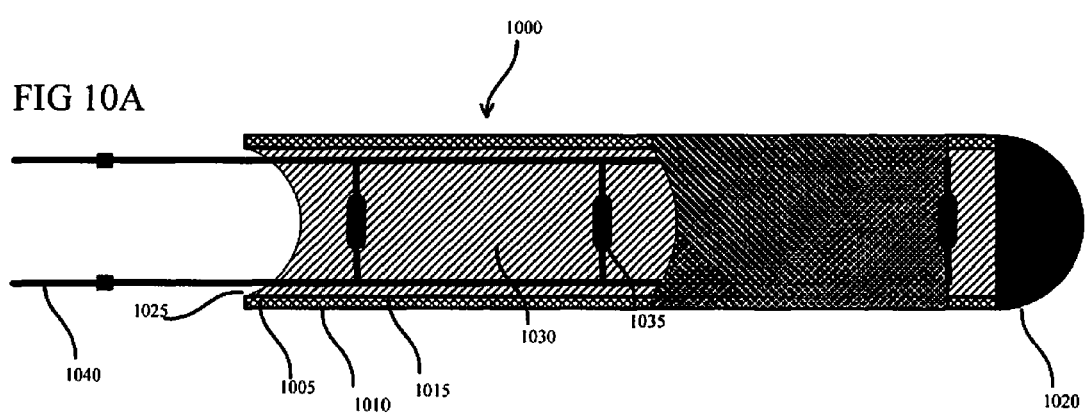
FIG. 10A illustrates a cross sectional view of an exemplary embodiment of the present invention.
Figure 10B:
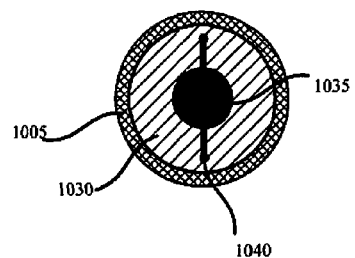
FIG. 10B illustrates another cross sectional view of an exemplary embodiment of the present invention.

Turning now to FIG. 10A, cross sectional view of guidewire 1000 is depicted. Guidewire 1000 comprises sheath 1005, which comprises outer surface 1010, inner surface 1015, and tip 1020. Sheath 1005 defines interior 1025, which houses core 1030. Guidewire 1000 is configured to be stiffened via activation of core 1030. For instance, core 1030 may comprise a material activated via mechanical stimulation, such as a non-Newtonian fluid. Such a material could be activated, for example, via oscillatory stimulation, stiffening guidewire 1000 while such mechanical stimulation is applied. As another example, core 1030 may comprise an electroactive material, such as an electroactive polymer or piezoelectric material, which may be activated via electrical stimulation, for instance from electrodes embedded in sheath 1005, coupled to inner surface 1015, or housed within interior 1025 (as illustrated via electrode 1040). Upon electrical stimulation, electroactive material comprising core 1030 is activated, operatively stiffening guidewire 1000. As another example, core 1030 may comprise intertwined coils activated via rotational force, or may comprise a biaxial braid activated via axial force, either of which, when activated, stiffen guidewire 1000. Other functional configurations will be apparent, and include combinations of the above, interspersed according to sections for stiffening appropriate portions of guidewire 1000. FIG. 10B depicts an axial cross section of guidewire 1000, illustrating that interior of sheath 1005 is filled with core 1030.

As can be understood, embodiments of the present invention provide guidewires having variable rigidity. The present invention has been described in relation to particular embodiments, which are intended in all respects to be illustrative rather than restrictive. Alternative embodiments will become apparent to those of ordinary skill in the art to which the present invention pertains without departing from its scope, including additional apparatuses, methods, and systems. Further, while embodiments have sometimes been described in relation to the surgical field, other uses will be apparent, such as whenever guidewires having variable rigidity may be useful. It should be noted that apparatuses, methods, and systems in accordance with embodiments may also be described as devices having components configured to implement such methods, or as computer-storage media or the like having instructions for causing devices to perform such methods. Likewise, systems in accordance with embodiments may be described according to the methods they perform.

From the foregoing, it will be seen that this invention is one well adapted to attain all the ends and objects set forth above, together with other advantages which are obvious and inherent to invention. It will be understood that certain features and subcombinations are of utility and may be employed without reference to other features and subcombinations. This is contemplated by and is within the scope of the claims.

The invention claimed is:
1. A guidewire comprising:
a core, comprising plurality of flexible elements;
a sheath disposed around the core, wherein the core and sheath are configured to be tightened together radially, and wherein tightening the sheath and the core together causes the flexible elements to interact, stiffening the guidewire.

2. The guidewire of claim 1, wherein the core and sheath are configured to be tightened together by tightening the sheath to the core.

3. The guidewire of claim 2, wherein the sheath is configured to be tightened to the core by applying suction.

4. The guidewire of claim 3, wherein the flexible elements are fibers.

5. The guidewire of claim 1, wherein the core and sheath are configured to be tightened together by tightening the core to the sheath.

6. The guidewire of claim 1, wherein the flexible elements are coiled together.

7. The guidewire of claim 1, wherein the flexible elements are braided together.

8. The guidewire of claim 1, wherein the core and sheath define a first section and a second section, and wherein the first section is configured to be tightened independently of the second section.

9. The guidewire of claim 1, wherein the flexible elements comprise a helically wound braid, and wherein the core is configured to be tightened to the sheath via applying axial force to the helically wound braid, causing the braid to expand radially to couple to the sheath.

10. The guidewire of claim 1, wherein the core comprises a coil defining an interior, wherein the interior houses a balloon, and wherein the core is configured to be tightened to the sheath via inflating the balloon.

11. A guidewire comprising:
a core, comprising a plurality of flexible elements;
a sheath disposed around the core; and
a means for tightening the core and the sheath together radially.

12. The guidewire of claim 11, wherein the guidewire further comprises a tip having an inner surface, and wherein the core is fixed to the inner surface of the tip.

13. The guidewire of claim 12, wherein the flexible elements comprises a coil, and wherein the core is configured to be twisted to expand the coil radially and tighten it to the sheath.

14. A guidewire comprising:
a first section;
a core extending through the first section, wherein the core comprises a coil configured to be expanded radially via twisting;
a sheath surrounding the core about the first section; and
the first section configured to increase in rigidity upon activation, wherein the activation comprises tightening the core and the sheath together by twisting, expanding the core radially.

15. The guidewire of claim 14, wherein the guidewire is configured to provide a pathway for an overlying element.

16. The guidewire of claim 14, further comprising a second section, the second section configured to increase in rigidity upon activation independently of the first section.

17. The guidewire of claim 14, wherein the sheath comprises an outer surface, the outer surface comprising a percutaneously compatible material.

18. The guidewire of claim 14, further comprising an element for twisting the core to cause activation.

19. The guidewire of claim 16, wherein the second section is configured for activation via radial expansion against the sheath.

20. The guidewire of claim 19, wherein the first section may be deactivated by counter-twisting, causing the coil to de-expand against the sheath, decreasing the rigidity of the first section.

* * * * *